United States Patent [19]

Heyward et al.

[11] Patent Number: 4,543,347

[45] Date of Patent: Sep. 24, 1985

[54] CATALYST COMPOSITION FOR CONVERSION OF SYNTHESIS GAS TO HYDROCARBONS

[75] Inventors: Malcolm P. Heyward, Camberley; Dennis Young, Staines, both of England

[73] Assignee: The British Petroleum p.l.c., London, England

[21] Appl. No.: 593,620

[22] Filed: Mar. 26, 1984

[30] Foreign Application Priority Data

Apr. 8, 1983 [GB] United Kingdom ............... 8309585

[51] Int. Cl.[4] .................... B01J 29/04; B01J 29/28
[52] U.S. Cl. ........................................ 502/61; 502/73; 502/74
[58] Field of Search ................. 502/61, 73, 64, 66, 502/74

[56] References Cited

U.S. PATENT DOCUMENTS 4,331,774  5/1982  Boersma et al. ............... 502/61 X
4,350,835  9/1982  Chester et al. ................ 502/61 X Primary Examiner—Carl F. Dees
Attorney, Agent, or Firm—Brooks Haidt Haffner & Delahunty

[57] ABSTRACT

The present invention relates to a catalyst composition suitable for converting synthesis gas to hydrocarbons which is a mixture of zinc oxide, an oxide of at least one metal selected from gallium and indium, an oxide of at least one additional metal selected from the elements of Group IB, II-V, VIB, VIIB and VIII including the Lanthanides and Actinides and a porous crystalline tectometallosilicate. The catalyst composition is formed by intimately mixing the tectometallosilicate and the mixture of metal oxides such that the individual particles have a size of less than 50 BSS mesh. The catalyst composition is particularly suited for converting synthesis gas to liquid, branched aliphatic hydrocarbons.

8 Claims, No Drawings

CATALYST COMPOSITION FOR CONVERSION OF SYNTHESIS GAS TO HYDROCARBONS

The present invention relates to a novel catalyst composition suitable for use in the conversion of synthesis gas to hydrocarbons, especially to aliphatic gasoline blending components.

Gallium containing catalyst compositions and the use thereof as hydrocarbon conversion catalysts are well known. These are claimed and described for example in our British Patent Specification Nos. 1496379, 1507549, 1507778, 1537780 and 1533169, and in our published European patent application Nos. 0024147 and 0024930. Amongst the various hydrocarbon conversion processes disclosed in these publications are dehydrogenation, dimerisation, isomerisation, cyclisation and aromatisation.

More recently in our copending published European Patent Specification No. 0070694 we have claimed and described a process for converting synthesis gas to hydrocarbons by contacting synthesis gas with a catalyst composition, characterised in that the catalyst composition comprises an oxide of at least one metal selected from gallium and indium, and contains an oxide of at least one additional metal selected from Group VIII and the B group elements of Groups I-VII including the Lanthanides and Actinides of the Periodic Table of Elements.

Zinc or zinc oxide containing catalysts compositions and the use thereof as synthesis gas conversion catalysts are well known. Examples include (i) mixed oxide compositions containing thorium and zinc for the production of isobutane and liquid hydrocarbons (Pichler, H and Ziesecke, K. H., "The Isosynthesis", U.S. Bureau of Mines Bulletin 488 (1950));

(ii) Copper oxide, zinc oxide and alumina for the production of methanol (e.g. French Pat. No. 2037567); and (iii) chromium and zinc oxides together with an aluminosilicate for the production of liquid hydrocarbons (e.g. U.S. Pat. No. 4292410).

It is also well known that porous crystalline tectometallosilicates, especially porous tectoaluminosilicates more widely known as zeolites, when used in conjunction with metal compounds which are active for conversion of synthesis gas can improve the performance of such metal compounds and/or change the product distribution. Porous crystalline tectometallosilicates have been especially useful in conjunction with appropriately active compounds, for high conversion processes to higher molecular weight hydrocarbons boiling in the gasoline and diesel ranges.

It has now been found that by using a specific combination of these catalytic components their overall performance in synthesis gas conversion can be improved.

Accordingly, the present invention is a novel catalyst composition suitable for converting synthesis gas to hydrocarbons comprising a mixture of zinc oxide, an oxide of at least one metal selected from gallium and indium, an oxide of at least one additional metal selected from the elements of Group IB, III-V, VIB, VIIB and VIII including the Lanthanides and Actinides of the Periodic Table of Elements and a porous crystalline tectometallosilicate.

The Periodic Table of Elements referred to herein is the Table appearing on pages 448 and 449 of the 44th Edition of the "Handbook of Chemistry and Physics", edited by Hodgman, C. D. and published by the Chemical Rubber Publising Co., Ohio, USA (1963).

The additional oxide is preferably that of at least one metal selected from copper, scandium, yttrium, lanthanum, titanium, zirconium, hafnium, chromium, molybdenum, tungsten, manganese, rhenium, iron, ruthenium, cobalt, rhodium, iridium, nickel, palladium, platinum, cerium, terbium, uranium and thorium, boron, aluminium, silicon, germanium, tin, lead, phosphorus, antimony and bismuth. Most preferred are copper, titanium, zirconium, hafnium, chromium, manganese, iron, ruthenium, cobalt, nickel, silicon, cerium, thorium and uranium.

Porous crystalline tectometallosilicates can be defined as compositions having a framework structure consisting of a rigid regular three-dimensional network of $SiO_4$ and $MO_4$ tetrahedra (where M is a metal atom) in which the tetrahedra are cross-linked by sharing the oxygen atoms such that the ratio of $(M+Si):O$ is 1:2. It has been claimed in the prior art that M can be Ti, Zr, V, Cr, Mo, Mn, Fe, Co, Rh, Ni, Zn, B, Al, Ga, Si, Ge, Sn, As and Sb or mixtures thereof, but in some cases the claimed materials have not been well characterised. In a special case where M=Si it refers to crystalline silicas. In some cases (e.g. where M has the formal oxidation state +4) the resultant framework is electroneutral and thus resembles crystalline silicas. In other cases there is a resultant negative charge on the framework which is neutralised by an electrochemical equivalent of cations. Porous crystalline tectometallosilicates have a structure which is sufficiently open to accommodate at least water molecules. A preferred group of porous tectometallosilicates for this invention are porous tectoaluminosilicates more generally referred to as zeolites. More preferably the zeolite should have a high silica to alumina ratio, i.e. greater than 5:1. Specific examples of such zeolites include those having the MFI structure type e.g. ZSM-5, the MEL structure type e.g. ZSM-11, the MOR structure type, and the zeolites known as ZSM-12, ZSM-23, ZSM-35, ZSM-38, zeolite beta and zeolite Theta-1. (MFI, MEL and MOR are examples from a nomenclature of structure types recommended by IUPAC in "Chemical Nomenclature, and Formulation of Compositions of Synthetic and Natural Zeolites", IUPAC Yellow Booklet, 1978; See also "Atlas of Zeolite Structure Types" by W. M. Meier and D. H. Olsen, International Zeolite Association, 1978). The zeolite is suitably in the dried hydrogen form free of organic materials, charge compensating cations except protons, and zeolitic water. Further treatments, e.g. metal loading, calcination in steam, oxidising or reducing treatments may also be carried out, if desired.

The catalyst compositions used in the present process are suitably prepared by mixing the respective components, e.g. the porous crystalline tectometallosilicate with a mixture of the metal oxide components. It is preferred that the mixing is intimate. By "intimate mixing" we mean that the individual particles of the metal oxide and crystalline tectometallosilicates are less than 50 BSS mesh and well mixed. The particles of the metal oxide and tectometallosilicate components are suitably less than 100 BSS mesh, preferably less than 200 BSS mesh in size.

The mixture of the metal oxides components used in the catalyst compositions is suitably prepared by mixing the respective compounds, for instance, by mixing a suspension of the respective compounds, e.g. the oxides, in water and evaporating the mixture to form a cake.

The cake may thereafter be filtered, washed and dried, and the dried cake crushed and calcined at elevated temperature to produce the desired catalyst composition.

Alternatively, the mixture of metal oxides used in the catalyst composition may be prepared by coprecipitation, for instance, by addition of a precipitating agent such as a soluble carbonate solution to a solution containing soluble salts of the respective metals in order to precipitate a mixed metal carbonate. The resultant solid may thereafter be filtered, washed and dried, and the resultant cake crushed and calcined at elevated temperatures as previously to produce the desired mixture of oxides.

Another suitable method for the preparation of the mixture of metal oxides is, for instance, by adding a precipitating agent to a slurry comprising a preformed mixed oxide of zinc and chromium and a clear aqueous solution of gallium nitrate, in order to precipitate a gallium-containing species onto the surface and/or into the pores of the preformed mixed oxide.

One particularly useful precipitation method is homogeneous precipitation whereby for example the precipitating agent is urea which on warming slowly hydrolyses releasing hydroxide ions which slowly precipitates gallium hydroxide thereby encouraging deposition of gallium oxide into the pores of the preformed mixed oxide. The resultant solid may thereafter be filtered, washed, dried into a cake, crushed and calcined at elevated temperatures as previously.

Another suitable method for the preparation of metal oxide mixtures is by impregnation in which a substrate to be impregnated is treated simultaneously or successively with a solution or solutions of the impregnant metal species so as to deposit the impregnant species on the surface of and/or into the pores of the substrate. The substrate impregnated may be one or more metal oxides, or an inert support. The substrate preferably has a high surface area. The impregnated substrate may thereafter be dried, crushed and calcined at elevated temperatures as previously to produce the desired mixture of oxides whether or not on a support. A combination of any of the above techniques may also be used.

In all the above methods of preparation of the mixed oxides the calcination is suitably carried out in an oxidising atmosphere, e.g. air.

The techniques for preparation of porous crystalline tectometallosilicates are well known. Usually, the as-prepared materials require further treatment to convert them into a catalytically active form. This may consist of well-known ion-exchange, washing, drying and calcination techniques. The tectometallosilicates may be subjected to further treatments, e.g. metal loading, calcination in steam and/or reducing atmospheres for optimum performance.

In the final catalyst composition, for optimum performance, the relative proportions of the mixed metal oxide and the porous crystalline tectometallosilicates will depend upon their relative activities. For instance, a relatively greater amount of porous aluminosilicates which have been steamed to modulate performance will be required than would be the case if the unsteamed material were used. Generally the combined amount by weight of the mixed metal oxides is suitably from 1 to 99%, preferably from 5 to 99%, and the amount by weight of the porous crystalline tectometallosilicate may be suitably be from 1 to 99%, preferably 1 to 95%. The relative atomic proportions of the various metals in the mixed oxides present in the final catalyst composition will depend upon the relative activities of the component oxides which in turn depend on inherent activity, number and position of available active sites and other factors known to those skilled in the art. These in turn depend on the method of preparation of the composition. It is suitably as follows: zinc from 1 to 95%, preferably from 3 to 85%, gallium and/or indium from 1 to 75%, preferably from 3 to 50%, and the additional metals from 4 to 98%, preferably from 20 to 94%.

The catalyst compositions of the present invention may be pelletised or extruded together with a binder prior to use. Such binders will be known to those skilled in the art. Examples of such binders include silica and alumina.

The catalyst compositions of the present invention may be activated or conditioned prior to use by methods known to those skilled in the art. Examples of such treatments include thermal treatments in oxidising or reducing atmospheres.

The catalyst compositions of the present invention show improved performance for the conversion of synthesis gas to hydrocarbons. Specifically, the combination of zinc oxide, an oxide of gallium and/or indium, the additional metal oxides and a porous crystalline tectometallosilicate show higher conversion of synthesis gas to liquid branched aliphatic hydrocarbons than analogous catalysts without the zinc oxide and at least an oxide of gallium or indium. Liquid, branched aliphatic hydrocarbons are useful for example as high quality gasoline blending stocks. They complement aromatic gasoline blending stocks which can be produced by the process claimed in our copending published European Patent Specification No. 0070694, in that they generally have a higher volatility and lower density.

A synthesis gas feedstock having a hydrogen to carbon monoxide ratio from 0.2:1 to 6:1 may be converted to hydrocarbons by passing over the catalyst composition of the present invention at a temperature suitably from 200° to 800° C., preferably from 300° to 600° C. most preferably from 350° to 475° C. The reaction pressure may be from 1 to 1000 bar, preferably from 30 to 300 bar most preferably from 30 to 100 bar. $CO/H_2$ space velocity can suitably vary from 100 to 20,000 preferably 500 to 10,000, most preferably from 1,000 to 5,000 GHSV (measured at STP) but, as will be clear to those skilled in the art, optimum GHSV will vary strongly according to e.g. temperature, pressure and $CO:H_2$ ratios. The products of this reaction are rich in hydrocarbons, especially in $C_5$–$C_{10}$ isoparaffins but are low in undesirable $C_1$–$C_2$ hydrocarbons.

EXAMPLE 1

(i) 24 g of thorium nitrate and 14.8 g zinc nitrate hexahydrate were dissolved in 400 ml distilled water. 17.2 g anhydrous sodium carbonate was dissolved in 200 ml distilled water. Both solutions were brought to the boil and the mixed nitrate solution added rapidly, with stirring to the carbonate solution. The precipitate so formed was filtered and washed with 15×80 ml water, and dried for 16 hours at 100° C. and calcined for 2 hours at 300° C. to form a mixed oxide of thorium and zinc.

(ii) To 5 g of the mixed oxide from (i) above was added 50 ml of a gallium nitrate solution (containing 0.025 g Ga/ml) at pH 2.9 and 10 g urea. This mixture was refluxed for 4 hours and the solid filtered and washed with 200 ml water, then dried for 16 hours at 100° C.

(iii) 5 g of the resultant solid from (ii) above was mixed with 5 g of crystalline MFI-type aluminosilicate having a silica to alumina ratio of about 35:1 and which had been previously converted to the hydrogen form by refluxing with 10% wt/wt nitric acid in water. The mixture was bound with 10 g Ludox AS40 (Regd. Trade Mark) colloidal silica (40% wt/wt in water). After drying for 16 hours at 100° C. the catalyst cake was crushed and sieved to a particle size between 12 and 30 mesh (BSS).

EXAMPLE 2

A mixed oxide of thorium, zinc and gallium was prepared as in Example 1(ii) above. To 2.5 g of the mixed oxide was added 2.5 g of chromic oxide (precipitated from a chromium trichloride solution with ammonia, dried and calcined at 560° C.) and mixed with 5 g of hydrogen-form crystalline MFI-type aluminosilicate ($SiO_2:Al_2O_3$ approximately 35:1 molar) and subsequently bound with silica as in Example 1(iii) above.

EXAMPLE 3

A mixed oxide of thorium, zinc and gallium was prepared as in Example 1(ii) above. To 2.5 g of the mixed oxide was added 2.5 g $SiO_2$ (Davison 57 grade) and 5 g of hydrogen-form crystalline MFI-type aluminosilicate ($SiO_2:Al_2O_3$ approximately 35:1 molar) and the mixture processed as in Example 1(iii) above.

Comparative Test 1

(not according to the invention)

To a 5 g sample of the mixed oxide of thorium and zinc prepared in Example 1(i) above was added 5 g of hydrogen-form crystalline MFI-type aluminosilicate having a silica to alumina ratio of above 35:1 and the mixture was bound with 10 g Ludox AS40 colloidal silica (40% wt/wt in water). After drying for 16 hours at 100° C., the catalyst cake was crushed and sieved to a particle size between 12 and 30 mesh (BSS).

Comparative Test 2

(not according to the invention)

29.4 g of zinc oxide were slurried in 80 ml distilled water. A solution of chromium (VI) trioxide (9.7 g $CrO_3$ in 22.6 ml water) was added dropwise to the zinc oxide slurry with continuous vigorous stirring. Stirring was continued for one hour after addition of chromium (VI) trioxide. The solid basic zinc chromate thus formed was filtered and dried for 16 hours at 100° C.

5 g of this basic zinc chromate was mixed with 2.5 g of hydrogen-form crystalline MFI-type aluminosilicate ($SiO_2:Al_2O_3$ approximately 35:1 molar) having a silica to alumina ratio of about 35:1 and the mixture bound with 15 g Ludox AS40 colloidal silica (40% wt/wt in water). After drying for 16 hours at 100° C. the catalyst cake was crushed and sieved to a particle size between 12 and 30 mesh (BSS).

EXAMPLE 4

To 5 g of the basic zinc chromate prepared as in Comparative Test 2 above was added 50 ml of a gallium nitrate solution (containing 0.025 g Ga/ml) at pH 2.9 and 10 g urea. This mixture was refluxed for 4 hours and the solid filtered and washed with 100 ml water and then dried for 16 hours at 100° C.

5 g of the resultant oxide mixture was mixed with 2.5 g of hydrogen-form crystalline MFI-type aluminosilicate ($SiO_2:Al_2O_3$ approximately 35:1 molar) and processed as in Example 1(iii) above.

Comparative Test 3

(not according to the invention)

A gallium oxide suspension was prepared by calcination of gallium nitrate at 600° C. for 16 hours and by slurrying 1.8 g of the resultant oxide in 200 ml of a solution containing thorium nitrate (24 g) dissolved in distilled water which was then heated to boiling. Another solution containing anhydrous $Na_2CO_3$ (9.5 g) in 200 ml distilled water was also heated to boiling and then added to the thorium nitrate solution to precipitate thorium oxide. The resultant solid was filtered while still hot, washed with 15×40 ml boiling distilled water and dried in an oven at 110° C. for 20 hours to form a cake of the mixed oxides of gallium and thorium. The cake was then crushed and sieved to a particle size smaller than 100 mesh (BSS). 5 g of the resultant powder was mixed thoroughly with 5 g of hydrogen-form MFI-type crystalline aluminosilicate ($SiO_2:Al_2O_3$ approximately 35:1 molar). This mixture was bound with 15 g Ludox AS40 colloidal silica (40 wt % in water) (LUDOX is a Registered Trade Mark). After drying for 20 hours at 110° C. the bound catalyst was crushed and sieved to a particle size of 8–30 mesh (BSS) before calcining in a slow stream of air at 300° C. for 4 hours.

EXAMPLE 5

A mixture of thoria, zinc oxide, gallia and the hydrogen form of a crystalline MFI-type aluminosilicate ($SiO_2:Al_2O_3$ ca 35:1) was prepared as in Example 1. In this case, however, the aluminosilicate was converted to the hydrogen form by ammonium exchange followed by calcination for 4 hours at 560° C. in a stream of air containing 20% vol/vol steam.

EXAMPLE 6

A mixture of thoria, zinc oxide, gallia and a crystalline MFI-type aluminosilicate ($SiO_2:Al_2O_3$ ca 35:1) was prepared as in Example 5.

EXAMPLE 7

A mixture of thoria, zinc oxide and gallia was prepared as in Example 1 (i) and (ii). 5 g of the thoria/zinc oxide/gallia mixture was mixed with 5 g of crystalline MFI-type gallosilicate ($SiO_2:Ga_2O_3$ ca 40) which had previously been converted to the hydrogen form by ammonium exchange followed by calcination for 2 hours at 400° C. in air. The mixture was bound with 10 g Ludox AS 40 (Registered Trade Mark) colloidal silica (40% wt/wt in water). After drying for 16 hours at 100° C. the catalyst cake was crushed and sieved to a particle size between 12 and 30 mesh (BSS).

EXAMPLE 8

A mixture of thoria, zinc oxide and gallia was prepared as in Example 1 (i) and (ii). 5 g of the thoria/zinc oxide/gallia mixture was mixed with 5 g of crystalline Theta-1 type aluminosilicate ($SiO_2:Al_2O_3$ ca 70, described in our published EP 57049) in the hydrogen form and pelleted by compressing the powder and then crushing and sieving to a particle size between 12 and 30 mesh (BSS).

10 ml each of catalysts from the Examples 1-8 and Comparative Tests 1-3 were separately loaded into a fixed bed reactor and tested for conversion of a mixture of CO and $H_2$ under the conditions specified in the Table below. In the cases of the catalysts from Example 4 and Comparative Test 2, after loading into the reactor and prior to testing for conversion of a CO and $H_2$ mixture, the catalysts were heated in the reactor at 325° C. in an atmosphere of hydrogen at 20 psig, flowing at 50 ml/min for 2 hours.

TABLE

| Catalyst | Example 1 | | Comparative Test 1 | Example 2 | Example 3 | | Example 4 | | Comparative Test 2 | Comparative Test 3 | Example 5 | | Example 6 | Example 7 | Example 8 |
|---|---|---|---|---|---|---|---|---|---|---|---|---|---|---|---|
| Temp (°C.) | 450 | 425 | 449 | 456 | 422 | 450 | 425 | 391 | 391 | 450 | 450 | 400 | 400 | 400 | 400 |
| Pressure (bar) | 50 | 50 | 50 | 50 | 50 | 50 | 50 | 50 | 50 | 50 | 50 | 50 | 50 | 50 | 50 |
| GHSV | 1980 | 1310 | 1990 | 2040 | 1070 | 2040 | 1070 | 2000 | 1970 | 2400 | 2000 | 2000 | 3057 | 3040 | 3040 |
| HOS | 0.25 | 4.0 | 0.25 | 0.6 | 2.6 | 0.5 | 3.0 | 0.67 | 0.83 | 11.5 | 5.0 | 205 | 205 | 205 | 0.5 |
| $H_2$/CO | 1 | 1 | 1 | 1 | 1 | 1 | 1 | 1 | 1 | 1 | 1 | 1 | 2 | 2 | 2 |
| CO Conv (%) | 35.4 | 39.6 | 11.8 | 36.9 | 47.5 | 43.5 | 51.5 | 43.6 | 35.4 | 51 | 48.1 | 34.1 | 29.7 | 32.2 | 36.2 |
| PRODUCTS[1] | | | | | | | | | | | | | | | |
| $C_1 + C_2$ | 4.90 | 3.27 | 2.58 | 2.88 | 2.98 | 3.92 | 5.11 | 3.57 | 2.52 | 3.5 | 2.74 | 0.78 | 2.19 | 2.62 | 5.47 |
| $C_3$ | 1.92 | 1.92 | 0.70 | 2.03 | 2.92 | 3.39 | 4.18 | 1.85 | 1.54 | } 10.2 | 2.41 | 1.06 | 1.26 | 2.22 | 3.06 |
| $C_4$ | 3.57 | 4.29 | 1.45 | 4.84 | 7.45 | 7.46 | 8.71 | 5.35 | 4.06 | | 7.17 | 4.16 | 3.67 | 2.38 | 3.18 |
| $C_5+$[2] | 8.48 | 11.62 | 1.24 | 9.67 | 12.19 | 10.11 | 11.04 | 11.24 | 9.27 | 3.0 | 12.12 | 8.90 | 10.08 | 12.92 | 9.92 |
| Aromatics | 0.55 | 0.96 | [3] | 0.92 | 0.83 | 0.90 | 0.97 | 2.66 | 0.80 | 9.8 | 2.74 | 2.22 | 1.45 | 1.25 | 1.75 |
| $CO_2$ | 15.96 | 17.50 | 5.88 | 16.62 | 21.13 | 17.75 | 21.45 | 18.94 | 17.19 | 24.5 | 20.92 | 16.91 | 11.05 | 10.79 | 12.79 |

[1] Mol % CO converted to a particular product
[2] excluding aromatics
[3] not detected
GHSV — Gas Hourly Space Velocity
HOS — Hours on Stream
Conv — Conversion Comparison of Example 1 with Comparative Test 1 shows the beneficial effects of adding gallium oxide to the catalyst, both in terms of increased conversion and increased selectivity to $C_5+$ hydrocarbons.

Likewise Example 4 and Comparative Test 2 illustrate the benefit in terms of increased conversion of adding gallium oxide to these catalyst compositions.

Comparison of Example 1 and Comparative Test 3 shows how the addition of ZnO to the catalyst composition greatly increases selectivity to aliphatic gasoline.

We claim:

1. A catalyst composition suitable for converting synthesis gas to hydrocarbons comprising a mixture of zinc oxide, an oxide of at least one metal selected from gallium and indium, an oxide of at least one additional metal selected from the elements of Group IB, III-V, VIB, VIIB and VIII including the Lanthanides and Actinides of the Periodic Table of Elements and a porous crystalline tectometallosilicate.

2. A catalyst composition according to claim 1 wherein the additional oxide is that of at least one metal selected from copper, scandium, yttrium, lanthanum, titanium, zirconium, hafnium, chromium, molybdenum, tungsten, manganese, rhenium, iron, ruthenium, cobalt, rhodium, iridium, nickel, palladium, platinum, cerium, terbium, uranium and thorium, boron, aluminium, silicon, germanium, tin, lead, phosphorus, antimony and bismuth.

3. A catalyst composition according to claims 1 or 2 wherein the porous tectometallosilicate has a silica to alumina ratio greater than 5:1 and is selected from those having the MFI structure type the MEL structure type, the MOR structure type, and the zeolites known as ZSM-12, ZSM-23, ZSM-35, ZSM-38 and zeolite beta.

4. A catalyst composition according to claim 1 or 2 wherein the combined amount by weight of the mixed metal oxides is from 1 to 99% and the amount by weight of the porous crystalline tectometallosilicate from 1 to 99%.

5. A catalyst composition according to claim 1 or 2 wherein the relative atomic proportions of the various metals in the mixed oxides present in the final catalyst composition is as follows: zinc from 1 to 95%, gallium and/or indium from 1 to 75% and the additional metals from 4 to 98%.

6. A catalyst composition according to claim 1 or 2 wherein the additional metal oxide is thorium oxide.

7. A process for producing a catalyst composition claimed in claim 1 wherein the porous crystalline tectometallosillicate and a mixture of the metal oxide components are intimately mixed such that the size of the individual particles of the metal oxide and crystalline tectometallosilicates are less than 50 BSS mesh.

8. A process according to claim 7 wherein the mixture of the metal oxide components used for producing the catalyst composition is prepared by addition of a precipitating agent to a solution containing the respective metals compounds in order to precipitate a mixed metal compound, the resultant solid precipitate being filtered, washed and dried, crushed and calcined at elevated temperatures to produce the desired mixture of the metal oxides.

* * * * *

UNITED STATES PATENT AND TRADEMARK OFFICE
CERTIFICATE OF CORRECTION

PATENT NO. : 4,543,347
DATED      : September 24, 1985
INVENTOR(S) : MALCOLM P. HEYWARD and DENNIS YOUNG It is certified that error appears in the above-identified patent and that said Letters Patent is hereby corrected as shown below:

On title page [73], "The British Petroleum p.l.c." should read --The British Petroleum Company p.l.c.--

Cols. 7-8, Table, Under Example 6, GHSV, "3057" should read --3058"

Cols. 7-8, Table, Under Example 5, HOS, "5.0   205" should read --5.0   2.5--

Cols. 7-8, Table, Under Examples 6 and 7, HOS, "205" should read --2.5--

Signed and Sealed this

Fourteenth Day of January 1986

[SEAL]

Attest:

Attesting Officer

DONALD J. QUIGG

Commissioner of Patents and Trademarks